United States Patent
Sahin

(10) Patent No.: US 9,554,795 B2
(45) Date of Patent: Jan. 31, 2017

(54) ANVIL CAP OF A MULTIPLE UMBRELLA TYPE FOR CIRCULAR STAPLERS

(71) Applicant: Mustafa Sahin, Konya (TR)

(72) Inventor: Mustafa Sahin, Konya (TR)

(*) Notice: Subject to any disclaimer, the term of this patent is extended or adjusted under 35 U.S.C. 154(b) by 406 days.

(21) Appl. No.: 14/200,722

(22) Filed: Mar. 7, 2014

(65) Prior Publication Data

US 2014/0291377 A1    Oct. 2, 2014

(30) Foreign Application Priority Data

Mar. 26, 2013 (TR) ................................ 2013/03634

(51) Int. Cl.
| | | |
|---|---|---|
| *A61B 17/072* | (2006.01) | |
| *A61B 17/068* | (2006.01) | |
| *A61B 17/11* | (2006.01) | |
| *A61B 17/115* | (2006.01) | |
| *A61B 17/00* | (2006.01) | |

(52) U.S. Cl.
CPC .......... *A61B 17/068* (2013.01); *A61B 17/072* (2013.01); *A61B 17/11* (2013.01); *A61B 17/115* (2013.01); *A61B 17/1155* (2013.01); *A61B 17/07207* (2013.01); *A61B 17/1114* (2013.01); *A61B 2017/00477* (2013.01); *A61B 2017/07214* (2013.01); *A61B 2017/07257* (2013.01)

(58) Field of Classification Search
CPC .............. A61B 17/068; A61B 17/072; A61B 17/07207; A61B 17/115; A61B 17/1155; A61B 17/1114; A61B 17/064; A61B 2017/072144; A61B 2017/07214

USPC ......................... 227/19, 175.1, 175.2, 176.1, 179.1,227/180.1; 606/139, 151, 153, 219
See application file for complete search history.

(56) References Cited

U.S. PATENT DOCUMENTS

| | | | | |
|---|---|---|---|---|
| 4,505,414 A | * | 3/1985 | Filipi ................... | A61B 17/115 227/155 |
| 4,700,703 A | * | 10/1987 | Resnick ............... | A61B 17/115 227/155 |
| 4,752,024 A | * | 6/1988 | Green .................. | A61B 17/115 227/19 |
| 5,197,649 A | * | 3/1993 | Bessler ............... | A61B 17/1114 227/156 |
| 5,732,872 A | * | 3/1998 | Bolduc ............... | A61B 17/0644 227/176.1 |
| 5,951,576 A | * | 9/1999 | Wakabayashi ..... | A61B 17/0644 227/175.1 |
| 7,080,769 B2 | * | 7/2006 | Vresh .................. | A61B 17/1114 227/176.1 |
| 7,694,866 B2 | * | 4/2010 | Shifrin ................ | A61B 17/115 227/179.1 |

(Continued)

FOREIGN PATENT DOCUMENTS

CN        201782789 U        4/2011

*Primary Examiner* — Scott A. Smith
(74) *Attorney, Agent, or Firm* — Egbert Law Offices, PLLC

(57) ABSTRACT

An anvil cap for providing secure anastomosis in a circular staplers in which the anvil cap has a movable inner shaft, a command wire connected to the movable inner shaft so as to cause a pulling movement to be applied to the movable inner shaft, a plurality of upper wings pivotally mounted to joint points on the movable inner shaft so as to be openable in relation to the movable inner shaft, and a plurality of lower wings cooperative with the plurality of upper wings such that the plurality of lower wings open when the plurality of upper wings apply pressure to the plurality of lower wings.

13 Claims, 4 Drawing Sheets

(56) References Cited

U.S. PATENT DOCUMENTS

| | | | | |
|---|---|---|---|---|
| 7,708,181 B2* | 5/2010 | Cole | ............... | A61B 17/115 |
| | | | | 227/175.2 |
| 7,975,895 B2* | 7/2011 | Milliman | ............ | A61B 17/115 |
| | | | | 227/175.1 |
| 8,066,723 B2* | 11/2011 | Suyker | ............. | A61B 17/0644 |
| | | | | 227/175.1 |
| 2002/0185517 A1* | 12/2002 | Vresh | ............. | A61B 17/1114 |
| | | | | 227/176.1 |

* cited by examiner

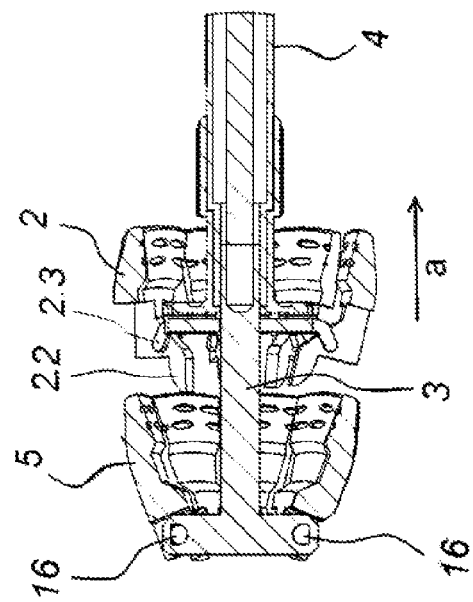
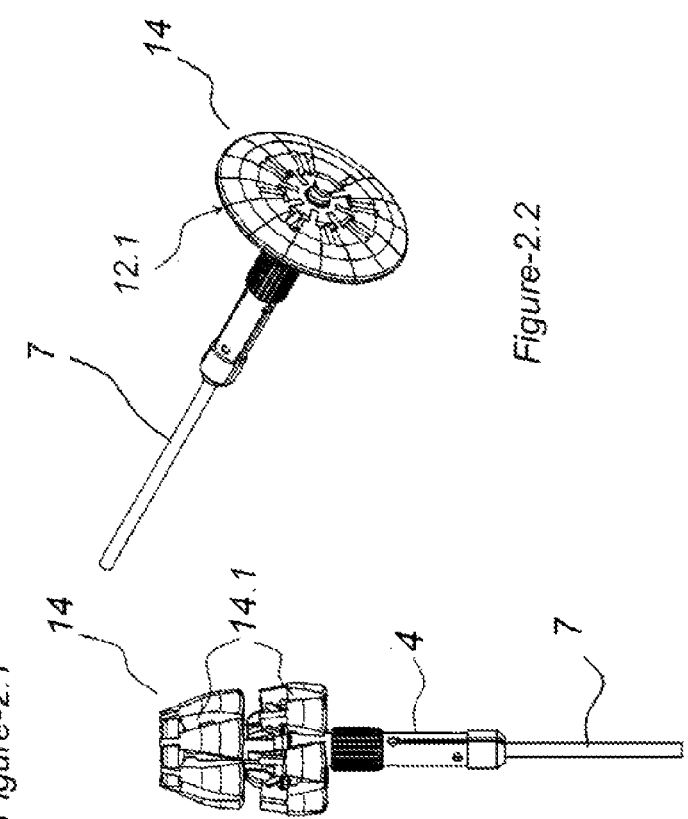
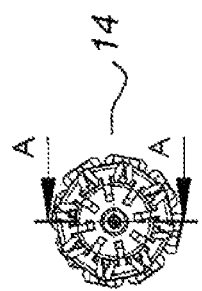

ANVIL CAP OF A MULTIPLE UMBRELLA TYPE FOR CIRCULAR STAPLERS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to the circular staplers used as automatic suturator in digestive system surgical operations.

The present invention especially relates to a foldable anvil cap of an umbrella type which makes it possible to conduct quick and secure anastomosis in providing the continuity of the circular stapler digestive system.

2. Description of Related Art Including Information Disclosed Under 37 CFR 1.97 and 37 CFR 1.98.

Currently, the staplers are composed of two parts: to main body (handle) and an anvil attached to the end part of said body. Even said circular staplers which are available in the market make it possible to conduct quick and secure anastomosis, it is very limited for them to be used especially in laparoscopic surgery because of several shortcomings. There are several major shortcomings limiting the area of use in both open and laparoscopic surgery.

First, a separate and large space is required to be formed on the bowel wall in order to locate the anvil into the bowel or stomach lumen that are going to be anastomosed, Second, it is difficult and time-wasting to close the open end with shining suture even if it is located through the open end of the bowel and the stomach (for instance locating into esophagus following total gastrectomy) in both open and laparoscopic surgery.

Third, in some cases (after esophagus surgery), the anvil is needed to reach the anastomsis line orally by being attached to the end of a catheter, as a result of which the microorganisms in the oral cavity and esophagus spread into the abdomen, and thus the risk of infection increases.

Said applications cause difficulty of use and waste of time, and they limit the area of use. For example, it is not possible to use the available stapler anvils by attaching them onto the endoscope ends, and such an example of usage is not available.

In the research conducted in relation with the prior art, an application numbered CN201782789 has been found. In this application, a trigger mechanism created on a main body, back-pull handle, a modular anvil, and an anvil cap are disclosed. The invention discloses a foldable and movable anvil cap which can pass from the horizontal position to the parallel position.

BRIEF SUMMARY OF THE INVENTION

In order to eliminate the disadvantages of the state of the art, an object of the present invention is that the anvil cap can be folded onto itself by being divided into triangle parts with fractions extending from two or more centers to the outer edge.

A further object of the present invention is that it can be made to go through a smaller space by reducing the surrounding area down to ½ and ⅓ of the diameter when it is open.

A further object of the present invention is that it can be produced in a detachable manner on the main body in a fixed or modular way (one-piece/modular), and go into the end that is going to be anastomosed through a small cut and conduct anastomosis by being opened in the shape of an umbrella mechanism inside the lumen.

Another object of the present invention is that there is no need for a separate bigger cut in order to locate it inside the lumen.

A further object of the present invention is that it eliminates the need for locating the shirring suture in order to close the space that it goes into.

A further object of the present invention is that it provides advantage in both open and laparoscopic interventions.

Another object of the present invention is to expand the area of use in laparoscopic surgery.

A further object of the present invention is to eliminate the need for anastomoses conducted by linear staplers and by locating suturs manually in laparoscopic surgery, and the difficulty of conducing manual anastomosis.

A further object of the present invention is to expand the laparoscopic surgery indications because of the ease of use of the stapler.

Another object of the present invention is to make it possible to apply various surgical interventions through the natural openings (NOTES—Nature Orifice Transluminal Endoscopic Surgery) of the body by being mounted to the end parts of endescopy systems (Gastroscope, colonoscope, sigmoidoscope).

The present invention developed to provide the above-mentioned advantages, relating to an anvil cap providing a secure anastomosis in the circular staplers in providing the continuity of the digestive system having a main body, and clamping arm, a stapler part and a stapler surface corresponding to this stapler part; characterized in comprising a movable inner shaft on which a pulling movement is applied by means of an operating cable, upper wings that are made to perform an opening movement by means of the hinge points of said movable inner shaft, lower wings that are opened after said upper wings are opened and the pulling movement is applied on the lower wings, supporting protrusions created on said movable inner shaft, locating spaces created between said supporting protrusions, connection space created on said lower wings, thrust bearing created on said lower wings, supporting protrusions having a locating space created the end part of said fixed outer shaft, connection spaces created on said upper wings, cable bearings created on said upper wings and the thrust protrusions created on said upper wings.

BRIEF DESCRIPTION OF THE SEVERAL VIEWS OF THE DRAWINGS

FIG. 2 is the two-dimensional side view of the anvil cap of an umbrella type according to the present invention when it is closed.

FIG. 2.1 is the two-dimensional front view of the anvil cap of an umbrella type according to the present invention.

FIG. 2.2 is the perspective view of the anvil cap of an umbrella type according to the present invention when it is open.

FIG. 2.3 is the A-A sectional view of the anvil cap described in FIG. 2.1.

DESCRIPTION OF THE REFERENCE NUMBERS

Figure 1:
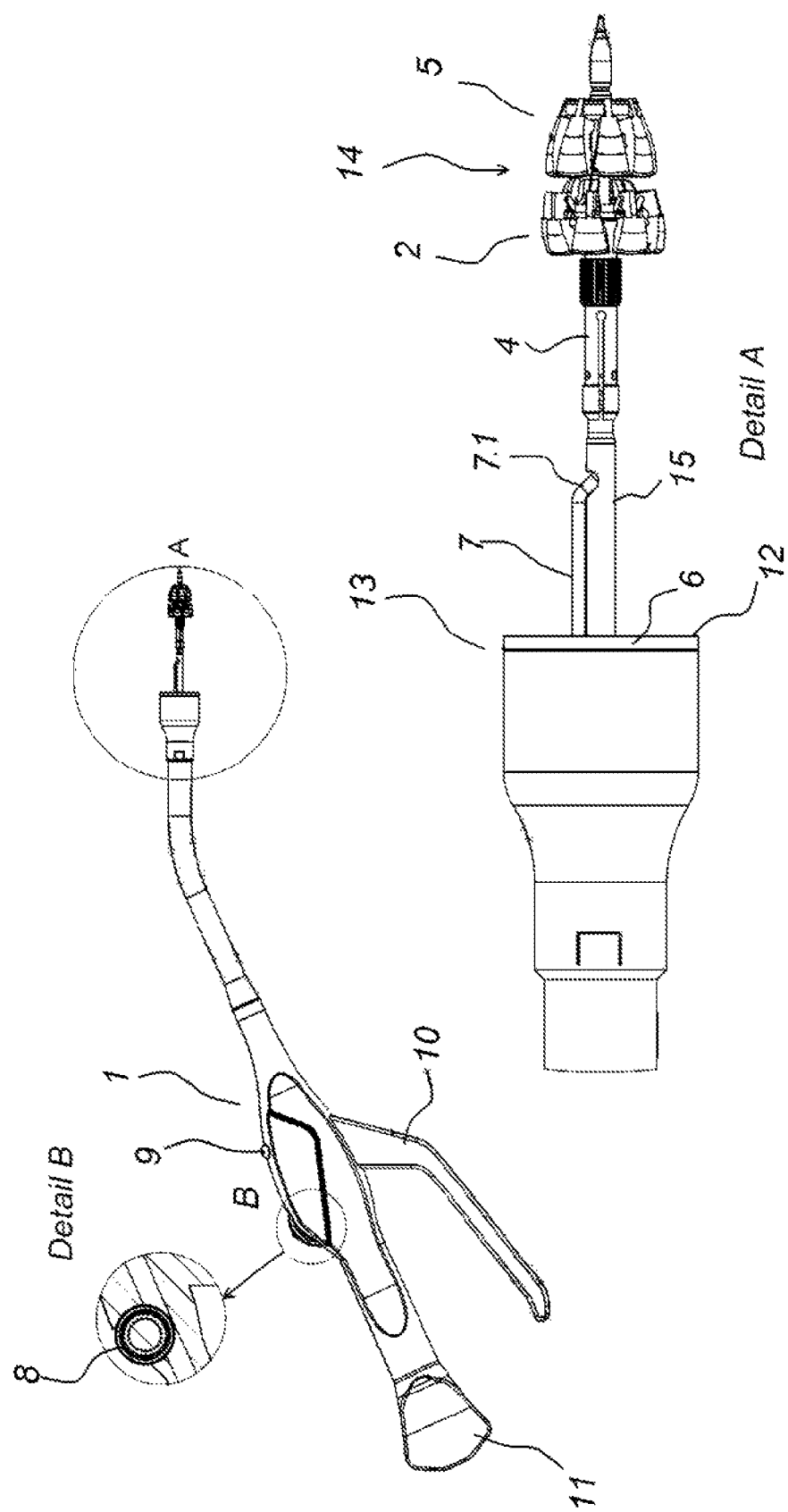
FIG. 1 is the two-dimensional and close a-detail side view of the circular staplers with anvil cap of umbrella type according to the present invention.
Figure 3:
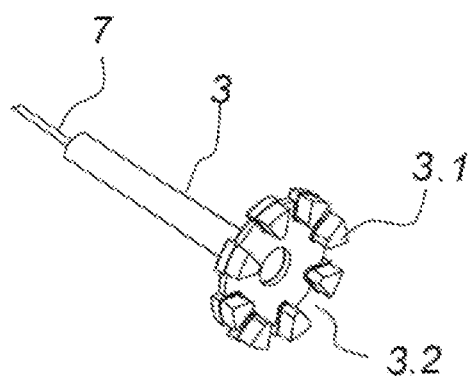
FIG. 3 is the general perspective view of the fixed outer shaft.
Figure 4:
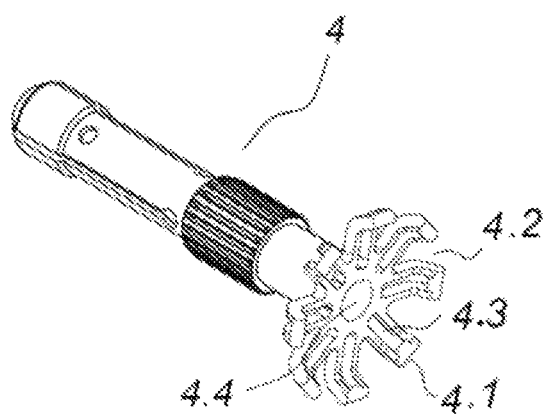
FIG. 4 is the view of the retaining protrusions together with the movable inner shaft.

1. Main body
2. Lower wings
2.1 Connection space
2.2 Thrust bearing
23 Joint point
3. Movable inner shaft
3.1 Retaining protrusion
3.2 Positioning space
4. Fixed outer shaft
4.1 Retaining protrusion
4.2 Positioning space
4.3 Mounting space
4.4 Crossing opening for the movable inner shaft
5. Upper wings
5.1 Connection space
5.2 Wire beating
5.3 Thrust protrusion
6. Blade mechanism
7. Command wire
7.1 Wire connection point
8. Wire wrap pulley
9. Pressure Control Section
10. Clamping arm
11. Shaft Withdrawing Arm
12. Punch section
12.1 Punch surface
13. Cartridge
14. Anvil cap
14.1 Interstitial spaces
15. Anvil movement shaft
16. Joint points

DETAILED DESCRIPTION OF THE INVENTION

The present invention relates to an anvil cap (14) providing secure anastomosis in the circular staplers while providing the continuation of the digestive system, and having a main body (1), a clamping arm (10) configured on said main body (1), punch section (12) and a punch surface (12.1) corresponding to said punch section (12); characterized in comprising movable inner shaft (3) on which a pulling movement is applied by means of a command wire (7), upper wings (5) which are made to open by means of the joint points (16) of said movable inner shaft (3), lower wings (2) which are made to open when said upper wings (5) apply a pressure on the lower wings (2) after they open and apply a pulling movement.

The present invention further comprises retaining protrusions (4.1) configured on said fixed outer shaft (4), mounting spaces (4.3) configured on said retaining protrusions (4.1) positioning spaces (4.2) configured between said retaining protrusions (4.1), connection space configured on said lower wings (2), thrust bearing (2.2) configured on said lower wings (2), retaining protrusions (3.1) comprising a positioning space (3.2) configured on the end part of said movable inner shaft (3), connection spaces (5.1) configured on said upper wings (5), wire bearings (5.2) configured on said upper wings (5) and thrust protrusions (5.3) configured on said upper wings (5).

In FIG. 1 and its a-detail, the general side view of the foldable anvil of an umbrella type according to the present invention is shown. In the figure, the steel wire wrap pulley (8) located on the command wire (7), pressure control section (9) showing the level of combination of the anvil according to the present invention with the cartridge (13), clamping arm (10) providing the textures to be punched as the staples inside the cartridge (13) go out and enabling the excess of the textures to be cut by operating the blade mechanism (6), shaft withdrawing arm (11) providing the anvil to be combined and locked with the cartridge (13) by making it closer to the stapler main body are shown.

In FIGS. 2, 2.1, 2.2 and 2.3, the drawings showing the sectional views of the anvil cap (14) of umbrella type according to the present invention are shown when it is in opened and closed position. In the figure, the fixed outer shaft (4) bearing the parts of the anvil cap (14) at the lower level combines the anvil with the stapler main body (1). The movable inner shaft (3) providing the downwards-upwards movements of the anvil and on said movable inner shaft (3), the upper wings (5) of the anvil cap (14) are located. The fixed outer shaft (4), command wire (7) providing the upper wings (5) to be open with the umbrella mechanism and that section to be lowered, the punch section (12) carrying the staplers are shown.

In FIGS. 2.2 and 2.3 the perspective and sectional views of the wings (2,5) of the anvil of an umbrella type according to the present invention are shown when they are in open and close position. In the Figures, the movable inner shaft (3) controlling the movements of the upper wings (5) of the anvil cap (14), and the command wire (7) providing the upper wings (5) to be open with the umbrella mechanism and that section to be lowered are shown.

Figure 5:
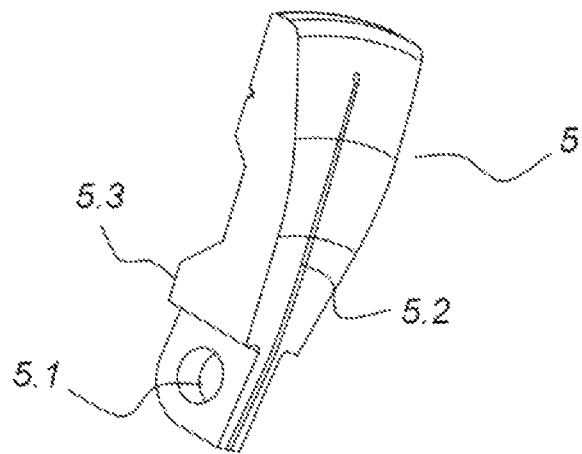
FIG. 5 is the close-shot separate perspective view of the upper wings.
Figure 6:
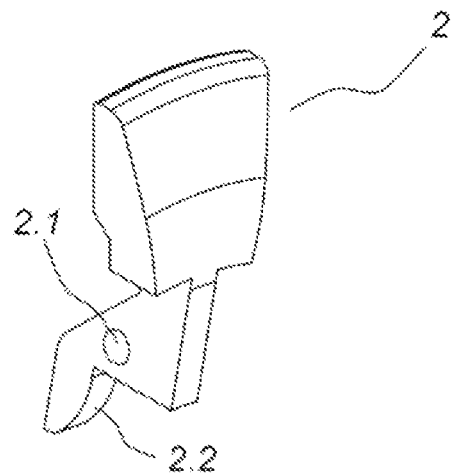
FIG. 6 is the close-shot separate perspective view of the lower wings.

In FIGS. 5 and 6, the perspective views of the wings (2, 5) of the anvil of an umbrella type according to the present invention are available. In the figures, the lower wing (2) is shown as one of the wings of the anvil cap (14) at the lower level, and the upper wings (5) is shown as one of the wings of the anvil cap (14) at the upper level.

In using the anvil according to the present invention, first of all, half of the divided parts of the anvil are fixed on the inner shaft (3) with the hinges by skipping one part and its other half which remains at a lower level is connected, by means of the hinges, with another fixed outer shaft (carrier shaft) (4) that the movable inner shaft (3) goes through (4.4). The upper parts (5) that are attached to the movable inner shaft (3) are located to a much upper level than the other parts (2) that are attached to the fixed outer shaft (4). The command wires (7) attached to the end parts of the parts available on an upper level are made to go through the fixed outer shaft (4), and it is combined (7.1) with the lower part (7) of the steel wire on the drawing shaft (15) available inside the main body (1) of the stapler, which makes the anvil closer to the cartridge.

By operating the said wrap pulleys (8), the command wire (7) is stretched and the upper wings (5) are made to change from close position to the open position, and they are pulled downwards at the same time. In the course of this pulling movement, the inclined parts on the lower surfaces of the upper wings (5) apply a pressure through the ends of the lower parts at the center, and these parts are provided to be open as an umbrella. After the umbrella mechanisms at both levels are open, the upper wings (5) are pulled downwards, and they are intertwined with the lower wings (2), and therefore the integrity of the anvil cap (14) is provided. After the anvil cap (14) opens entirely, the shaft is made to approach to the cartridge part by means of the withdrawing arm (11), and the anastomosis process is conducted by tightening the clamping arm (10).

The working principle of the anvil cap (14) having an opening structure like an umbrella is as follows; a pulling movement is applied in a-direction to the movable inner shaft (3) by means of the command wire (7), the upper wings (5) are connected to the movable inner shaft (3) by means of the joint points (16) in a way that they can move, the upper wings (5) are approached to the lower wings (2) in a-direction by applying a pulling movement to said movable inner shaft (3), said upper wings (5) applies a pressure on the thrust bearing (2,2) of the lower wings (2) and an opening movement is provided to the lower wings (2) by means of the joint point (2.3), and said lower wing (2) and the upper wings (5) are located into the interspaces, and therefore the anvil cap (14) is configured. Therefore, as the lower wings (2) and the upper wings (5) open in the form of an umbrella, a punch surface (12.1) is obtained.

I claim:

1. An anvil cap for providing secure anastomosis in a circular stapler, the circular stapler having a main body with a clamping arm affixed thereto and a punch section having a punch surface thereon, the anvil cap comprising:
    a movable inner shaft;
    a command wire connected to said movable inner shaft so as to cause a pulling movement to be applied to said movable inner shaft;
    a plurality of upper wings pivotally mounted to joint points on said movable inner shaft, said plurality of upper wings being openable in relation to said movable inner shaft; and
    a plurality of lower wings cooperative with said plurality of upper wings such that said plurality of lower wings open when said plurality of upper wings apply pressure to said plurality of lower wings.

2. The anvil cap of claim 1, further comprising:
    a plurality of retaining protrusions defining a positioning space at an end portion of said movable inner shaft.

3. The anvil cap of claim 1, said plurality of lower wings having a connection space thereon.

4. The anvil cap of claim 1, said plurality of lower wings having a thrust bearing thereon.

5. The anvil cap of claim 1, further comprising:
    a fixed outer shaft having retaining protrusions thereon.

6. The anvil cap of claim 5, said retaining protrusions defining mounting spaces on said fixed outer shaft.

7. The anvil cap of claim 5, said fixed outer shaft and said retaining protrusions having positioning spaces therebetween.

8. The anvil cap of claim 5, said fixed outer shaft having a crossing opening at an upper end thereof, said crossing opening receiving said movable inner shaft.

9. The anvil cap of claim 5, said plurality of lower wings being connected by joint points to said fixed outer shaft so as to open in relation thereto.

10. The anvil cap of claim 1, said plurality of upper wings having connection spaces thereon.

11. The anvil cap of claim 1, said plurality of upper wings having wire bearings connected thereto.

12. The anvil cap of claim 1, said plurality of upper wings having thrust protrusions thereon.

13. A method of using an anvil cap to provide secure anastomosis in a circular stapler in which the circular stapler has a main body and a clamping arm affixed to the main body and a punch section having a punch surface thereon, the method comprising:
    connecting a plurality of upper wings to a movable inner shaft via first joint points such that said plurality of upper wings are pivotable in relation to the movable inner shaft;
    connecting a plurality of lower wings to a fixed outer shaft via second joint points such that said plurality of lower wings are pivotable in relation to said fixed outer shaft;
    applying a pulling movement to said movable inner shaft via a command wire so as to move said plurality of upper wings toward said plurality of lower wings;
    applying a pressure onto a thrust bearing of said plurality of lower wings by said plurality of upper wings so as to open said plurality of lower wings; and
    locating said plurality of lower wings and said plurality of upper wings to interspaces.

* * * * *